United States Patent [19]

Mazzenga et al.

[11] Patent Number: 5,073,539

[45] Date of Patent: Dec. 17, 1991

[54] TRANSDERMAL ADMINISTRATION OF ZWITTERIONIC DRUGS

[75] Inventors: Gerard C. Mazzenga, New City; Bret Berner, Scarsdale, both of N.Y.

[73] Assignee: Ciba-Geigy Corporation, Ardsley, N.Y.

[21] Appl. No.: 468,388

[22] Filed: Jan. 22, 1990

[51] Int. Cl.$^5$ ............................................. A61K 31/00
[52] U.S. Cl. ........................................ 514/2; 514/946; 424/449
[58] Field of Search ..................... 514/2, 946; 424/449

[56] References Cited

U.S. PATENT DOCUMENTS 4,575,503  3/1986  Watthey .............................. 514/213
4,866,160  9/1989  Coy et al. ............................. 514/15

Primary Examiner—John Doll
Assistant Examiner—E. J. Kraus
Attorney, Agent, or Firm—Irving M. Fishman

[57] ABSTRACT

Compositions of zwitterionic drugs for transdermal administration and methods of administering zwitterions transdermally are disclosed. The compositions comprise a zwitterionic drug in a salt form and a solvent therefor.

14 Claims, No Drawings

TRANSDERMAL ADMINISTRATION OF ZWITTERIONIC DRUGS

FIELD OF THE INVENTION

The present invention relates to the area of transdermal administration of drug substances. It further relates to the area of zwitterionic drugs and methods of making such drugs transdermally administrable.

BACKGROUND OF THE INVENTION

Zwitterionic drugs have poor absorption through intact skin due to their rather large dipole moments and their resulting low lipid solubility. In general, salts of organic compounds have lower skin permeation than their corresponding free acids or bases. The unionized acids and bases can take advantage of lipophilic pathways through the skin that ionic species cannot. Typical non-zwitterionic acidic or basic substances can be placed in transdermal formulations at appropriate pHs such that the active agent is substantially in the nonionic form leading to enhanced absorption through human skin.

Unfortunately, zwitterionic drugs cannot be made non-ionic. At all pHs, at least one ionic group is present. For example, at pHs higher than the pKa of the acidic group(s) of a zwitterion, the acidic group is charged; at pHs lower than the pKa of the basic group(s) of a zwitterion, the basic group is charged. At pHs close to the zwitterion pI, both groups are charged. Amino acid containing drugs, being the zwitterions of greatest interest, remain charged at all pHs in the range of 2.0 to 11 suitable for transdermal application. It would not be expected that one could achieve a suitable flux of a zwitterion through skin to make transdermal administration thereof practical.

A number of transdermal devices are disclosed in the following U.S. Patents, all of which are incorporated herein by reference: U.S. Pat. Nos. 4,605,670, 3,551,554, 4,677,131, 3,472,931, 4,132,781, 4,557,943, 4,130,667, 3,952,099, 4,046,886, 4,299,826, 4,764,379, 4,379,454, 4,144,317, and 3,948,262 to name a few.

OBJECTS OF THE INVENTION

One object of the present invention is to provide a composition having a zwitterionic active species which can be suitably administered transdermally.

Another object of the invention is to provide a method of administering zwitterionic drugs transdermally.

Still another object is to provide transdermal devices containing zwitterionic agents for absorption at efficacious doses.

SUMMARY OF THE INVENTION

Surprisingly, these and other objects can be realized by a composition of a zwitterionic active species which comprises the zwitterionic active agent in a salt form.

DETAILED DESCRIPTION OF THE INVENTION

The present invention resides in the fact that contrary to the low transdermal flux that would be expected from zwitterionic species regardless of pH, these drugs have much improved flux through skin when a salt form of the zwitterion is selected. The present invention teaches that certain salts of zwiterionic drugs uniquely have lower melting points than the parent zwitterion, higher solubility in essentially all solvents than the parent zwitterion, including solvents such as octanol(a model of skin lipids), and consequently higher transdermal fluxes (see Table I).

The zwitterionic materials within the scope of the invention include, without limitation: amino acids, peptides, polypeptides, proteins, baclofen, CGS 16617, ACE Inhibitors, etc., especially, baclofen, CGS 16617, and benazeprilat.

The salt forms of the zwitterions that are suitable for use in the instant invention include the stoichiometric salt of the zwitterionic species with another entity having an acidic hydrogen and the resulting anion is not itself a zwitterion or an entity which is a suitable hydrogen acceptor group which is not a zwitterion. Alternatively, a cationic counterion may be selected. Particularly suitable are hydrohalide, especially hydrofluoride, hydrochloride, or hydrobromide; lower alkyl sulfonate, such as methane sulfonate or ethane sulfonate; dicarboxylate, such as the maleate; and the alkali metal salts, such as the lithium or potassium salts. The hydrogen receptors most desirable for use in the invention include hydroxides, carbonates, and bicarbonates. Specifically useful anions include acetate, benzenesulfonate, benzoate, bicarbonate, bitartrate, bromide, calcium edetate, camphorsulfonate, carbonate, chloride, citrate, dihydrochloride, edetate, ethanedisulfonate, laurylsulfate, ethanesulfonate, fumarate, glucoheptonate, glycollamidophenylarsonate, hexylresorcinate, hydrabamine, hydrobromide, hydrochloride, hydroxynaphthoate, iodide, hydroxyethanesulfonate, lactate, lactobionate, malate, maleate, mandelate, mesylate, methylbromide, methylnitrate, methylsulfate, mucate, napsylate, nitrate, pamoate, pantothenate, phosphate, diphosphate, polygalacturonate, salicylate, stearate, subacetate, succinate, sulfate, tannate, tartrate, and triethiodide. Specifically useful cations include benzathine, chlorprocaine, choline, diethanolamine, ethylenediamine, methylglucamine, procaine, aluminum, calcium, lithium, magnesium, potassium, sodium, and zinc. Still other counteranions of use in the present invention include: adipate, alginate, anhydromethylenecitrate, aspartate, bisulfate, butylbromide, camphorate, digluconate, dihydrobromide, disuccinate, glycerophosphate, hemisulfate, hydrofluoride, hydroiodide, methylenebissalicylate, naphthalenedisulfonate, oxalate, pectinate, persulfate, phenylethylbarbiturate, picrate, propionate, thiocyanate, tosylate, and undecanoate. Additional countercations include: benethamine, clemizole, diethylamine, piperazine, tromethamine, barium and bisimuth.

Within the above-mentioned classes, for a given zwitterion, the greater the counterions polarizability, the greater its charge distribution and the lesser its rigidity, the better the counterion is for the purposes of the present invention. The general trend guidelines are generally true within homologous series of counterions.

It is believed, without limiting the invention to that belief, that the salt formation in the manner described by the present invention results in a conversion of a large dipole moment in a free zwitterion into a much smaller one in the salt form allowing the molecule to take advantage of skin permeation pathways which would otherwise be foreclosed as a rsult of the increased solubility of the salt in both plar and nonpolar media.

The pH of the composition need only be maintained at a point which will maintain the integrity of the zwitterion/counter-ion salt association. Preferably, this pH is at least 1 pH unit away from the zwitterion's isoelectric point, more preferably at least 2 pH units from the zwitterion's isoelectric point. Advantageously, the pH range that is suitable for use in the invention is from about 2.0 to about 11.0, preferably about 3.0 to about 10, more preferably about 3.5 to about 9.0, still more preferably about 4.0 to about 8.5. Most preferably, the pH is maintained at or greater than the $pK_a$ of the zwitterion's basic group or at or below the $pK_a$ of the zwitterion's acidic group. More preferably, the pH is at least 0.5 pH units, more preferably at least 1.0 pH units, still more preferably at least 1.5 pH units and most preferably at least 2.0 pH units from the relevant $pK_a$.

The composition may also contain other optional ingredients which will further enhance the delivery of the desired species. Such optional items include, without limitation, additional flux enhancers, preservatives, stabilizers, buffers, thickeners, carriers and fillers, which are compatible with the requisite pH range and selection of counterion outlined by the present invention.

A solvent for the active species is also usually present; however, if the active agent or its salt is a liquid, then a solvent is not really necessary. In some instances, a solvent may also act as a flux enhancer. Typical solvents for use in the instant invention include, without limitation; water; $C_1$–$C_{10}$ alkanols such as ethanol, propanol, isopropanol, propylene glycol, glycerol, and other hydrogen bonding solvents, such as DMSO, dimethylformamide, ethyl acetate, fatty acid esters, pyrrolidones such as 2-pyrrolidone, N-(2-hydroxyethyl)-pyrrolidone, and N-methylpyrrolidone, lactams, polyalkanols, azones and carboxylic acids. When solvents are present, they are generally mixtures of water with at least one non-water solvent mentioned above. These mixtures may be from 3% to 97%, preferably 20% to 80%, more preferably 20% to 60% non-aqueous solvent component.

The compositions of the instant invention contain the salt form of the zwitterionic agent, which may be formed in situ, in an amount which would deliver a therapeutically effective amount thereof over a period of time. Such amounts can be readily determined from the length of time the zwitterion is to be administered, the flux thereof through the skin and surface, the size of the transdermal layers which separate the drug depot from the skin size of the contact area of the transdermal with the patient, etc, all of which would be readily within the abilities of one of ordinary skill in the art.

The formulation can be prepared according to standard formulating techniques available to those skilled in the relevant art. The formulation can be placed into a transdermal device by the same techniques used for loading any other transdermal device with drug formulation.

Having fully described the instant invention, the following non-limiting examples are presented to more clearly set it forth.

In the examples, the solubilities of free zwitterion and enhanced solubilities of various salts thereof are reported in various degrees in the following solvents: water, ethanol, octanol, chloroform and human stratum corneum. Permeation rates are also shown for these zwitterionic compounds and enhanced fluxes of the salts thereof through materials including polyurethane. While such materials are impractical for transdermal devices for free zwitterions, these materials are practical for the transdermal delivery of salts of zwitterions. The solubility in water is given as a model of polar solvents, while the octanol and chloroform are given as models for skin lipids. The critical factor for inclusion of a salt within the invention is that relative to its non salt zwitterion parent compound, the salt form of the invention has a greater solubility in both polar and lipid skin models.

TABLE 1.

Ex. Salt Enhancement

G. Mazzenga; B. Berner:
Table 1. Zwitterionic compounds and corresponding salts

| Compound | mp deg C. | Solubility in water at 25 deg. C. (ug/ml) | R.E.* | Solubility in ethanol at 25 deg. C. (ug/ml) | R.E.* | Solubility in octanol at 25 deg. C. (ug/ml) | R.E.* | Solubility in chloroform at 25 deg. C. (ug/ml) | R.E.* |
|---|---|---|---|---|---|---|---|---|---|
| Phenylalanine (Phe) | 285 | 25321.8 | 1.00 | 234 | 1.00 | 12.3 | 1.00 | 0.21 | 1.00 |
| Phe. hydrofluoride | 254 | 24837.4 | 0.98 | 411.66 | 1.76 | 52.24 | 4.25 | 0.29 | 1.38 |
| Phe. hydrochloride | 240 | 129008.6 | 5.09 | 24053.91 | 102.79 | 2601.4 | 211.50 | 1.61 | 7.67 |
| Phe. hydrobromide | 230 | 959690.8 | 3.78 | 107145.9 | 457.89 | 40231.8 | 3270.88 | 58.26 | 277.43 |
| Phe. hydroiodide | d > 38 | | | | | | | | |
| Baclofen (Bac) | 206 | 6828.7 | 1.00 | 1144.1 | 1.00 | 22.2 | 1.00 | 0.22 | 1.00 |
| Bac. methane sulfonate | 137 | 8826.9 | 1.29 | 170840 | 149.32 | | | 0.087 | 0.40 |
| Bac. ethane sulfonate | 140 | 38889.8 | 5.70 | 237181 | 207.31 | | | 11.17 | 50.77 |
| Bac. propane sulfonate | 166 | 24425.7 | 3.58 | 107317 | 93.80 | | | 8.74 | 39.73 |
| Bac. pentane sulfonate | 144 | | | 61650.3 | 53.88 | 576.4 | 25.96 | 37.4 | 170.00 |
| Bac. lithium salt | 214 | 21719.1 | 3.18 | 57837.3 | 50.55 | | | 6.93 | 31.50 |
| Bac. sodium salt | 252 | 21379.7 | 3.13 | 529056 | 462.42 | | | 3.47 | 15.77 |
| Bac. potassium salt | 181 | | | | | | | | |
| Bac. hydrofluoride | 159 | 1396.2 | 0.20 | 1790.88 | 1 | | | 0.104 | 0.4727 |
| Bac. hydrochloride | 195 | 244622.5 | 35.82 | 37498.9 | 32.78 | 324.3 | 14.61 | 5.34 | 24.27 |
| Bac. hydrobromide | 174 | 351946.8 | 51.54 | 129569.7 | 113.25 | 477.05 | 21.49 | 13.7 | 62.27 |
| Bac. maleate | 178 | 1292.3 | 0.19 | | | | | 0.026 | 0.1182 |
| Bac. fumarate | 154 | 1187.5 | 0.17 | | | | | 0.627 | 2.85 |
| Bac. nitrate | 199 | | | | | | | | |
| diBac. hydrophosphate | 158 | | | | | | | | |
| CGS 16617 | 218 | 491500 | 1 | 190.7 | 1 | 23.36 | 1 | | |
| CGS 16617. monomaleate | 144 | 623900 | 1.26 | 248.82 | 1.30 | 13.96 | 0.5976 | | |
| CGS 16617. dihydrochloride | 201 | 1127800 | 2.29 | 1890.75 | 9.91 | 87.8 | 3.759 | | |
| CGS 16617. dihydrobromide | 183 | 1423000 | 2.9 | 45026.9 | 235.90 | 506.7 | 21.69 | | |
| Benazeprilat (CGS14831) | 264 | | | 120.89 | 1.00 | | | | |
| CGS 14831. dilithium salt | 172 | | | 27975.61 | 231.41 | | | | |
| CGS 14831. dipotassium salt | d > 161 | | | 34193.51 | 282.85 | | | | |
| CGS 14831. dicesium salt | 145 | | | | | | | | |

G. Mazzenga; B. Berner;
Table 1. Zwitterionic compounds and corresponding salts

| Compound | mp deg C. | Solubility in poly-urethane (ug/ml) × 10⁻³ | R.E.* | Solubility in 35% ethyl vinyl acetate (ug/ml) × 10⁻³ | R.E.* | Permeation rate through poly-urethane (ug/cm 2/hr) | R.E.* | Solubility in human stratum corneum (ug/ml) | R.E.* | Permeation rate through human epidermis (ug/cm 2/hr) | R.E.* |
|---|---|---|---|---|---|---|---|---|---|---|---|
| Phenylalanine (Phe) | 285 | | | | | 1.92 | 1.00 | | | 1.02 | 1.00 |
| Phe. hydrofluoride | 254 | | | | | 4.68 | 2.44 | | | 2.14 | 2.10 |
| Phe. hydrochloride | 240 | | | | | 335.9 | 174.95 | | | 64.37 | 63.11 |
| Phe. hydrobromide | 230 | 1516.23 | 789.70 | | | 77.53 | 76.01 | | | | |
| Phe. hydroiodide | d > 38 | | | | | | | | | | |
| Baclofen (Bac) | 206 | 1.95 | 1.00 | | | 5.32 | 1.00 | 3.11 | 1.00 | 0.118 | 1.00 |
| Bac. methane sulfonate | 137 | 10.96 | 5.62 | | | 287.9 | 54.12 | | | | |
| Bac. ethane sulfonate | 140 | 21.90 | 11.23 | | | 211.9 | 39.83 | | | | |
| Bac. propane sulfonate | 166 | 11.60 | 5.95 | | | 233.9 | 43.97 | | | | |
| Bac. pentane sulfonate | 144 | | | | | 220.2 | 41.30 | | | | |
| Bac. lithium salt | 214 | 28.90 | 14.82 | | | 128.3 | 24.12 | | | | |
| Bac. sodium salt | 252 | 12.00 | 6.15 | | | 605.3 | 113.78 | | | | |
| Bac. potassium salt | 181 | 42.40 | 21.74 | | | 587.8 | 110.49 | | | | |
| Bac. hydrofluoride | 159 | 1.1 | 0.564 | | | 3.45 | 0.65 | | | | |
| Bac. hydrochloride | 195 | 178 | 91.28 | | | 273.7 | 51.45 | 22.15 | 7.12 | | |
| Bac. hydrobromide | 174 | 640 | 328.2 | | | 738.9 | 138.89 | 214.69 | 69.03 | 25.49 | 216.02 |
| Bac. maleate | 178 | 1.05 | 0.5385 | | | 19.13 | 3.59 | 292.2 | 93.95 | | |

TABLE 1.-continued

| | | | | | | | |
|---|---|---|---|---|---|---|---|
| Bac. fumarate | 154 | | | | | | |
| Bac. nitrate | 199 | 1.47 | 0.7538 | | 11.4 | 2.14 | |
| diBac. hydrophosphate | 158 | | | | | | |
| CGS 16617 | 218 | 0.0039 | 1 | 0.0048 | 1 | 0.538 | 1.00 |
| CGS 16617. monomaleate | 144 | 0.0105 | 2.69 | 0.0156 | 3.25 | 3.47 | 6.45 |
| CGS 16617. dihydrochloride | 201 | 0.0084 | 2.15 | 0.042 | 8.75 | 13.34 | 24.80 |
| CGS 16617. dihydrobromide | 183 | 0.29 | 74.35 | 0.336 | 70 | 65.31 | 121.39 |
| Benazeprilat (CGS14831) | 264 | | | | | 0.311 | 1.00 |
| CGS 14831. dilithium salt | 172 | | | | | 47.76 | 153.57 |
| CGS 14831. dipotassium salt | d > 161 | | | | | 75.01 | 241.19 |
| CGS 14831. dicesium salt | 145 | | | | | | |

| | | |
|---|---|---|
| | 0.1409 | 1.00 |
| | 8.95 | 63.52 |
| | 20.56 | 145.92 |

*Relative enhancement
Average of values measured in triplicate.

As is readily apparent, the salt form of the zwitterionic substance is generally more soluble than the free zwitterion in the solvent with the one exception of baclofen methane sulfonate in chloroform. Furthermore, the salt forms all have much greater permeation rates through polyurethane than free zwitterion. Finally, of the test conducted, the zwitterionic salts have significantly greater fluxes through stratum corneum and epidermis than their free zwitterion counterparts.

What we claim is:

1. A transdermal device for the administration of a pharmaceutically acceptable zwitterionic active agent to an animal in need thereof comprising a resevoir for said active agent, said active agent in salt form in a transdermally effective amount, and a pharmaceutically acceptable carrier for said active agent, wherein said pharmaceutically acceptable zwitterionic active agent is selected from the group consisting of amino acids, baclofen, and ACE Inhibitors, said pharmaceutically acceptable zwitterionic active agent and said carrier being in said reservoir.

2. The transdermal device of claim 1 wherein the salt form of said zwitterionic active agent is selected from the group consisting of hydrohalide, lower alkyl sulfonate, lower alkyl dicarboxylate, and alkali metal salt.

3. The trandermal device of claim 1 wherein said carrier is selected from the group consisting of water, $C_1$-$C_{10}$alkanols, and other hydrogen bonding solvents.

4. The transdermal device of claim 1 further comprising at least one of an additional flux enhancer for the zwitterionic active agent, a pharmaceutically and transdermally acceptable buffer, a thickener, a preservative and a filler.

5. The transdermal device of claim 1 wherein the pH is maintained at least one pH unit away from the isoelectric point of said zwitterionic active agent.

6. A method of administering a zwitterionic active agent to an animal in need of such administration comprising applying to said animals skin a transdermal device according to claim 1.

7. The composition of claim 1 wherein said active agent is benazeprilat.

8. The composition of claim 1 wherein the melting point of the zwitterionic salt is below that of the parent free zwitterion.

9. The composition of claim 1 wherein the solubility in a hydrogen bonding solvent of the zwitterionic salt is greater than that of the parent free zwitterion.

10. The composition of claim 1 wherein the solubility in octanol or chloroform of the zwitterionic salt is greater than that of the parent free zwitterion.

11. The composition of claim 9 wherein the solubility in octanol or chloroform of the zwitterionic salt is greater than that of the parent free zwitterion.

12. The composition of claim 8 wherein the solubility in a hydrogen bonding solvent of the zwitterionic salt is greater than that of the parent free zwitterion.

13. The composition of claim 8 wherein the solubility in octanol or chloroform of the zwitterionic salt is greater than that of the parent free zwitterion.

14. The composition of claim 12 wherein the solubility in octanol or chloroform of the zwitterionic salt is greater than that of the parent free zwitterion.

* * * * *

UNITED STATES PATENT AND TRADEMARK OFFICE
CERTIFICATE OF CORRECTION

PATENT NO. : 5,073,539

DATED : December 17, 1991

INVENTOR(S) : GERARD C. MAZZENGA, AND BRET BERNER

It is certified that error appears in the above-identified patent and that said Letters Patent is hereby corrected as shown below:

Column 10:

In each of claims 7-14, line 1, change "composition" to --transdermal device---

Signed and Sealed this

Seventeenth Day of August, 1993

Attest:

BRUCE LEHMAN

Attesting Officer

Commissioner of Patents and Trademarks